(12) United States Patent
Wright et al.

(10) Patent No.: US 9,205,419 B2
(45) Date of Patent: Dec. 8, 2015

(54) LARGE PORE METAL ORGANIC FRAMEWORKS

(75) Inventors: Paul A. Wright, North Haugh (GB); Michael T. Wharmby, North Haugh (GB); John P. S. Mowat, North Haugh (GB)

(73) Assignee: University Court of the University of St Andrews (GB)

( * ) Notice: Subject to any disclaimer, the term of this patent is extended or adjusted under 35 U.S.C. 154(b) by 245 days.

(21) Appl. No.: 13/878,752

(22) PCT Filed: Oct. 11, 2011

(86) PCT No.: PCT/GB2011/001464
§ 371 (c)(1),
(2), (4) Date: Jul. 8, 2013

(87) PCT Pub. No.: WO2012/049451
PCT Pub. Date: Apr. 19, 2012

(65) Prior Publication Data
US 2013/0296162 A1 Nov. 7, 2013

(30) Foreign Application Priority Data

Oct. 11, 2010 (GB) .................................. 1017095.9

(51) Int. Cl.
*B01J 20/22* (2006.01)
*B01J 31/16* (2006.01)
*B01J 31/22* (2006.01)
*B01D 53/04* (2006.01)
*C07F 9/59* (2006.01)
(Continued)

(52) U.S. Cl.
CPC ............... *B01J 31/22* (2013.01); *B01D 53/04* (2013.01); *B01J 20/226* (2013.01); *B01J 31/1691* (2013.01); *C07F 9/591* (2013.01); *C07F 13/005* (2013.01); *C07F 15/025* (2013.01); *C07F 15/045* (2013.01); *C07F 15/065* (2013.01); *B01D 2253/204* (2013.01)

(58) Field of Classification Search
CPC ...... B01J 20/226; B01J 31/1691; B01J 31/22; C07F 13/005; C07F 15/025; C07F 15/045; C07F 15/065; C07F 9/591; B01D 53/02; B01D 53/04; B01D 2253/204
USPC ................. 95/90, 900, 902; 96/108; 423/210; 210/660; 502/167, 401; 546/6
See application file for complete search history.

(56) References Cited

U.S. PATENT DOCUMENTS

| 5,648,508 A | 7/1997 | Yaghi et al. |
| 2007/0068389 A1* | 3/2007 | Yaghi ............................... 96/148 |

(Continued)

FOREIGN PATENT DOCUMENTS

WO WO 2009/049208 A1 4/2009

OTHER PUBLICATIONS

Shimizu et al. "Phosphonate and sulfonate metal organic frameworks", Chem. Soc. Rev., (2009), 38, pp. 1430-1449.*
Groves et al., "The first route to large pore metal phosphonates", Chemical Communications, No. 31, pp. 3305-3307 (2006).
Groves et al., "A route to large pore metal phosphonates-supplementary information", Supplementary Material (ESI) for Chemical Communications, Online Article, Retrieved from the internet: URL:http://www.rsc.org/suppdata/cc/b6/b605400e/b605400e.pdf, pp. 1-11, (2006).

(Continued)

*Primary Examiner* — Frank Lawrence
(74) *Attorney, Agent, or Firm* — Susan T. Evans; McDermott Will & Emery LLP (57) ABSTRACT

The present invention relates to novel micro or mesoporous metal organic frameworks (MOFs) which contain as ligands piperidine based phosphonic acids, as well as a method of synthesizing such MOFs and uses of the MOFs themselves.

18 Claims, 7 Drawing Sheets

(51) Int. Cl.
*C07F 13/00* (2006.01)
*C07F 15/02* (2006.01)
*C07F 15/04* (2006.01)
*C07F 15/06* (2006.01)

(56) References Cited

U.S. PATENT DOCUMENTS

2008/0121105 A1* 5/2008 Schubert et al. ............... 95/139
2009/0183996 A1* 7/2009 Richter et al. ............... 205/424

OTHER PUBLICATIONS

International Search Report from related PCT Patent Application No. PCT/GB2011/001464 mailed on Mar. 6, 2012, application now published as WO/2012/049451 on Apr. 19, 2012.

Miller and Wright "Nanoporous metal phosphonates", Encyclopedia of Inorganic Chemistry, John Wiley & Sons, Ltd., Chichester UK, ISBN: 9780470862100, pp. 1-14, Published Online Mar. 15, 2009.

* cited by examiner

LARGE PORE METAL ORGANIC FRAMEWORKS

CROSS REFERENCE TO RELATED APPLICATIONS

This application is a U.S. National Stage of International Patent Application No. PCT/GB2011/001464, filed Oct. 11, 2011, which claims the benefit of priority to GB Application No. 1017095.9, filed Oct. 11, 2010, each of which is hereby incorporated by reference in its entirety.

FIELD OF INVENTION

The present invention relates to novel micro or mesoporous metal organic frameworks (MOFs), as well as a method of synthesising such MOFs and uses of the MOFs themselves.

BACKGROUND TO THE INVENTION

The preparation of crystalline microporous solids with pore openings greater than 1 nm has long been an important target for those interested in the adsorption, separation and catalytic conversion of large organic molecules. Aluminosilicate zeolites with such large pores, which could be used in the catalytic refining of the heavy fraction of crude oil, have not yet been prepared. The synthesis of metal organic frameworks with pore openings larger than 1 nm does not suffer from the same restrictions on the required tetrahedral geometry of framework components experienced by zeolites, and consequently structures with pore openings above 1 nm (and cages well into the mesoporous regime (>2 nm)) have already been prepared. One of the approaches by which extra large pore MOF solids can be prepared is via isoreticular synthesis, where ligands of increasing dimensions but the same coordination geometry can, under suitable conditions, form solids with the same framework topology but with different dimensions (and consequently pore sizes and pore window sizes). The IRMOF series of zinc carboxylates built from linear dicarboxylates is one example. (O. M. Yaghi, M. O'Keeffe, N. W. Ockwig, H. K. Chae, M. Eddaoudi, and J. Kim, *Nature*, 2003, 423, 705-714).

The presence of coordinatively unsaturated metal sites (CUS) in some MOFs is an important structural feature, particularly for considerations of chemisorption and catalysis. These are usually produced when solvent molecules coordinated to framework metal cations are removed by heating, leaving the framework intact but the metal cations without a full sphere of coordinating ligands. Examples of carboxylate MOFs that contain five-fold CUS upon desolvation include CPO-27 (Fe, Mn, Mg, Co and Ni). (P. D. C. Dietzel, R. E. Johnsen, R. Blom, H. Fjellvag, *Chem. Eur.-J.*, 2008, 14, 2389-2397). Such coordinatively unsaturated metal sites are of much current interest as sites for adsorption of polar molecules or as Lewis acid sites in catalysis.

We have recently shown that it is possible to prepare large pore metal phosphonate MOFs which possess coordinatively unsaturated sites when dehydrated. The STA-12 series of divalent metal N,N'-piperazinebis(methylenephosphonate) materials, prepared with Mn, Fe, Co, and Ni in cation positions (FIG. 1), (J. A. Groves, S. R. Miller, S. J. Warrender, C. Mellot-Draznieks, P. Lightfoot and P. A. Wright *Chem. Commun.*, 2006, 3305-3307; S. R. Miller, G. M. Pearce, P. A. Wright, F. Bonino, S. Chavan, S. Bordiga, I. Margiolaki, N. Guillou, G. Ferey, S. Bourrelly and P. L. Llewellyn, *J. Am. Chem. Soc.*, 2008, 130, 15967-15981) has a pore size of 0.9 nm when dehydrated, and ca. 5 mmol g$^{-1}$ of five-fold coordinated metal sites that are able to interact as Lewis acids with molecules such as CO and acetonitrile. However, the size of pore limits the potential application of such metal phosphonate MOFs.

It is amongst the objects of the present invention to obviate and/or mitigate at least one of the aforementioned disadvantages.

SUMMARY OF THE INVENTION

In a first aspect there is provided a porous isoreticular metal organic framework (MOF) comprising an organic compound co-ordinated to at least one metal selected from Co, Ni, Mg, Mn, Fe, Zn, Cd and/or Ru, wherein the organic compound is of the formula $$PO_3CH_2X—Y—XCH_2PO_3$$

Wherein X is a substituted or unsubstituted heterocyclic amine containing one or more amine groups and Y forms a link between each group and may be a single bond, or a —(CH$_2$)$_n$— group (n≥1) or a —C≡C— group or a cyclic or heterocyclic substituted or unsubstituted ring structure.

Conveniently the metal is a single metal. Preferably the metal is Co, Ni, Mn, Mg or Fe. Similar materials containing mixtures of these metals in framework sites can also be prepared.

X may be a fully saturated heterocyclic amine ring structure and may preferably be based on a piperidine ring.

One or more available atoms on X may be substituted by a C$_1$-C$_4$ alkyl, hydroxy, amino, nitro, halo(bromo, chloro, iodo)

When Y is a cyclic or heterocyclic substituted or unsubstituted ring structure, it is to be understood that this forms a rigid link between the two X groups. A suitable linking structure may be a benzene ring. Typical substituents include nitro, amino, halo (bromo, chloro, iodo).

It is to be understood that the organic compounds of the present invention are generally symmetrical in order that the isoreticular structure can easily be formed. The term reticular is understood to mean having the form of net or netlike structure and "isoreticular" is therefore defined as being a net or netlike structure having the same network topology.

Figure 2:
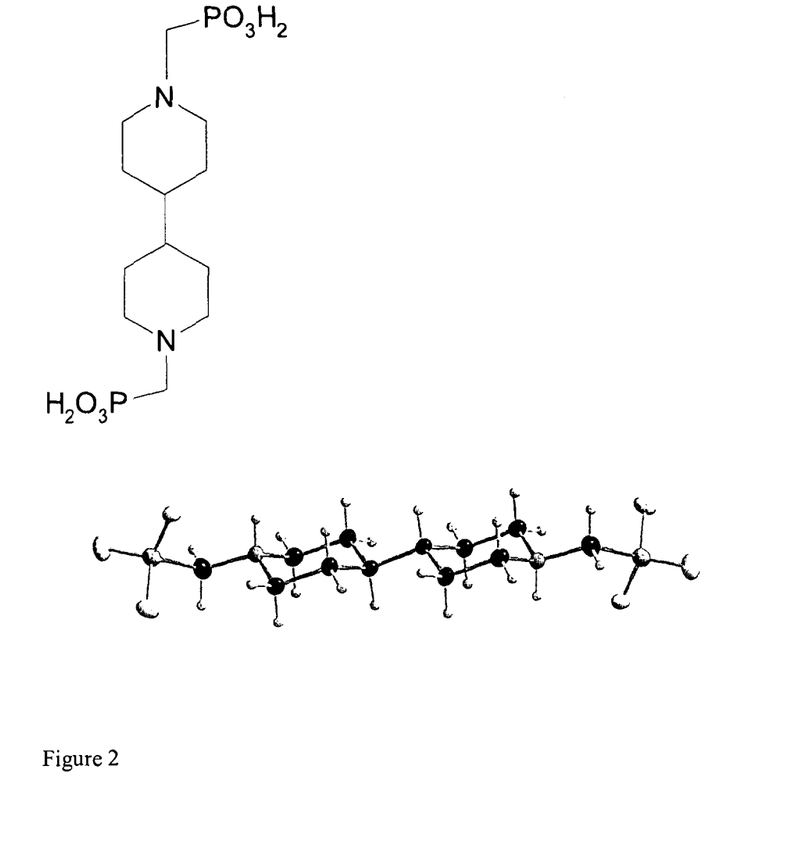
FIG. 2 shows a line drawing (left) and configuration in the crystalline solid (right) of one molecule of the 4,4'-N,N'-bipiperidinylbis(methylenephosphonic acid). In the line drawing all non-C—H protons are drawn on the phosphonate groups, whereas in the crystal structure two out of four non C—H protons are located on the piperidine N atoms and the other two were not located.

Most preferably the organic compound is 4,4'-N,N'-bipiperidinylbis(methylenephosphonate), as shown in FIG. 2.

The MOFs of the present invention are designed to have large regular pore structures of at least 1.5 nm in diameter, as measured by crystallography and N$_2$ adsorption at 77 K, preferably at least 1.7 nm and some may have pores greater than 2 nm in diameter and hence can be considered as mesoporous.

Moreover, the MOFs of the present invention due to their large pore size preferably have a porosity of at least 0.5 cm$^3$ g$^{-1}$, such as 0.6 cm$^3$ g$^{-1}$ or even higher.

In a further aspect, there is provided a method of making a MOF in accordance with the present invention, the method comprising the step of reacting a suitable base with at least one type of divalent metal cation and an organic acid of the formula $$H_2PO_3CH_2X—Y—XCH_2PO_3H_2$$

Wherein X and Y are previously defined above, under hydrothermal reaction conditions, in order to form a MOF according to the present invention.

Hydrothermal reaction conditions are known to the skilled addressee and generally involves applying high temperatures (typically 150-220° C.) and high autogeneous vapour pressures to cause crystallisation of a desired product.

A suitable base is sodium or potassium hydroxide, which is added in a sufficient amount to adjust the pH of the solution and to assist dissolution of the acid form of the ligand.

Typical molar ratios of the starting materials are: Metal salt bisphosphonic acid:base (MOH, M=Na, K):$H_2O$=0.5-2:1: 0.5-2:1000-1500

The MOFs so formed will generally include a solvent and/or water which may easily be removed by heating or dehydration techniques known to the skilled addressee.

The MOFs of the present invention may be further processed to form powders or aggregates of desired particle size, or may be shaped into pellet, pills, granules or the like. The MOFs may be mixed with other materials, such as binders, lubricants or other additives.

The MOFs of the present invention may be used for a variety of applications such as the uptake of one or more substances for the purpose of storage, separation, controlled release or chemical reaction and also as a support material for metals, metal oxides, metal sulphides, metal complexes, including metalloporphyrins or other materials and for use in catalysis.

Conveniently said one or more substances includes gases or liquids, as well as drug molecules.

The present invention will now be further described by way of example and with reference to the figures which show:—

BRIEF DESCRIPTION OF THE DRAWINGS

Table 1 Gives a list of X-ray Powder Diffraction Peaks of STA-16(Co), measured in transmission mode using Fe $K_\alpha$ radiation ($\lambda$=1.936042 Å), and showing d-spacings, $2\theta$ values and approximate relative intensities

We considered the use of 4,4'-N,N-bipiperidinylbis(methylenephosphonate) as an organic linker (see FIG. 2), written $H_4LL$. The corresponding phosphonic acid was therefore prepared via the modified Mannich reaction of bipiperidine with phosphorous acid and formaldehyde in a similar way to that adopted successfully for the preparation of N,N'-piperazinebis(methylenephosphonic acid) and its 2-methyl and 2,5-dimethyl analogues (J. P. S. Mowat, J. A. Groves, M. T. Wharmby, S. R. Miller, Y. Li, P. Lightfoot, P. A. Wright *J. Solid State Chem.* 2009, 182, 2769-2778). Details of the synthesis and characterisation of this ligand are given below. Single crystal X-ray crystallography of the structure indicates the molecule adopts a conformation (FIG. 2) that is similar to that required for isoreticular synthesis, with both rings in chair configuration, and a centre of symmetry on the C—C bond linking the two rings, as required in the STA-12 structure.

A series of hydrothermal synthesis was performed with divalent metal cations, using the reactant mixture composition $M(OAc)_2$:$H_2LL$:NaOH:$H_2O$=2:1:2:1000. Exemplary details are shown below.

Figure 3:
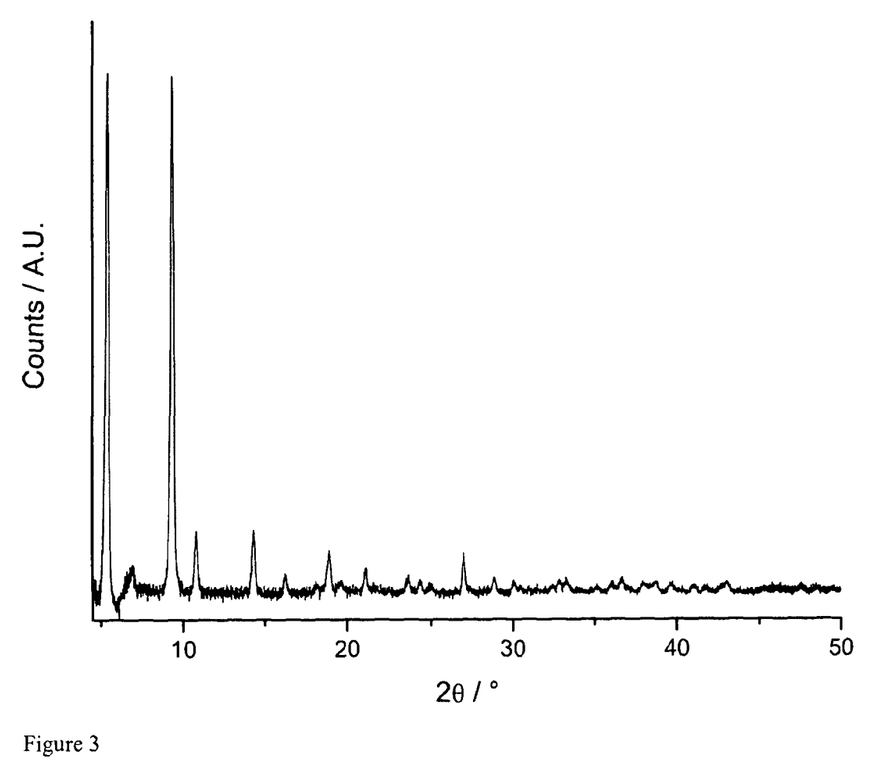
FIG. 3 shows X-ray pattern of STA-16(Co) measured using Fe K$\alpha$ radiation, $\lambda$=1.936 Å).

Addition of base was performed to control the pH and to help solubilise the ligand. In syntheses with $Co(OAc)_2$, a microcrystalline powder was obtained (and later established to be phase pure) with a characteristic X-ray powder diffraction pattern (FIG. 3). This was indexed using a rhombohedral cell (R-3, hexagonal setting, a=42.3 Å, c=6.24 Å) and named STA-16(Co) (St Andrews microporous material number 16). TGA analysis of STA-16(Co) in flowing air at 5° C./min indicates water loss which was complete by 150° C., followed by a plateau until 250° C., after which thermal decomposition of the solid occurs. EDX analysis indicated a Co:P ratio of 1.0 and combination of TGA and elemental analysis suggested a composition of $Co_2(H_2O)_9LL$, where LL=$C_{12}H_{22}N_2P_2O_6$. (Expected C=22.8%, N=4.4%; observed C=22.94%, N=4.26%.)

Figure 4:
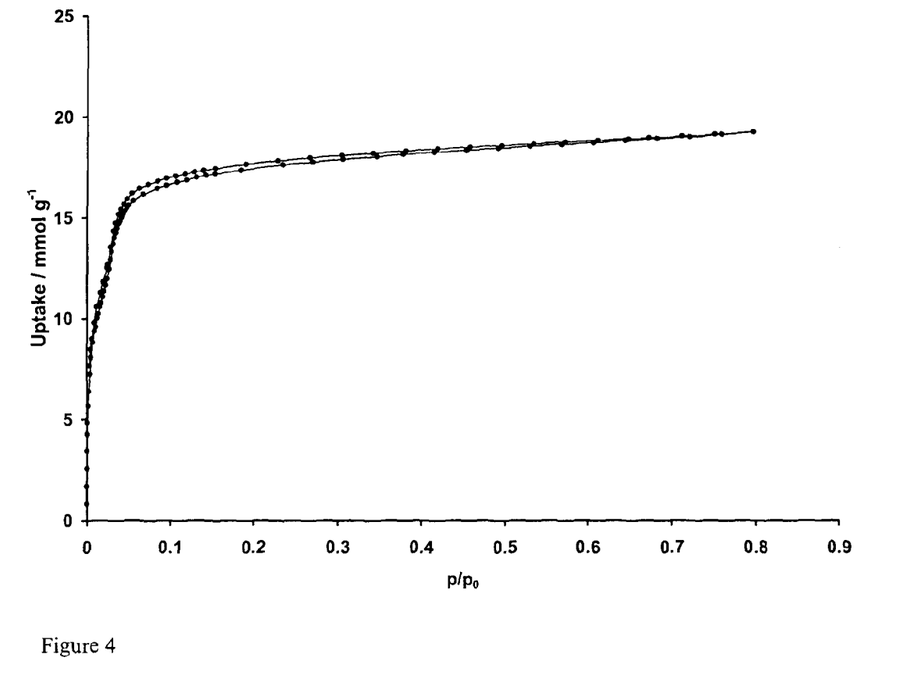
FIG. 4 shows adsorption and desorption branches of the $N_2$ adsorption isotherm measured on STA-16(Co) at 77 K.

The adsorption isotherm of $N_2$ at 77 K measured on STA-16(Co) pre-treated at 120° C. in vacuo is given in FIG. 4. The isotherm shape is consistent with an extra large pore solid (inflexion at $p/p_o$=0.03 indicating pore size approaching 2 nm) with a pore volume of 0.62 $cm^3$ $g^{-1}$ (compared to a pore volume of 0.20 $cm^3$ $g^{-1}$ for STA-12(Ni)).

Figure 1:
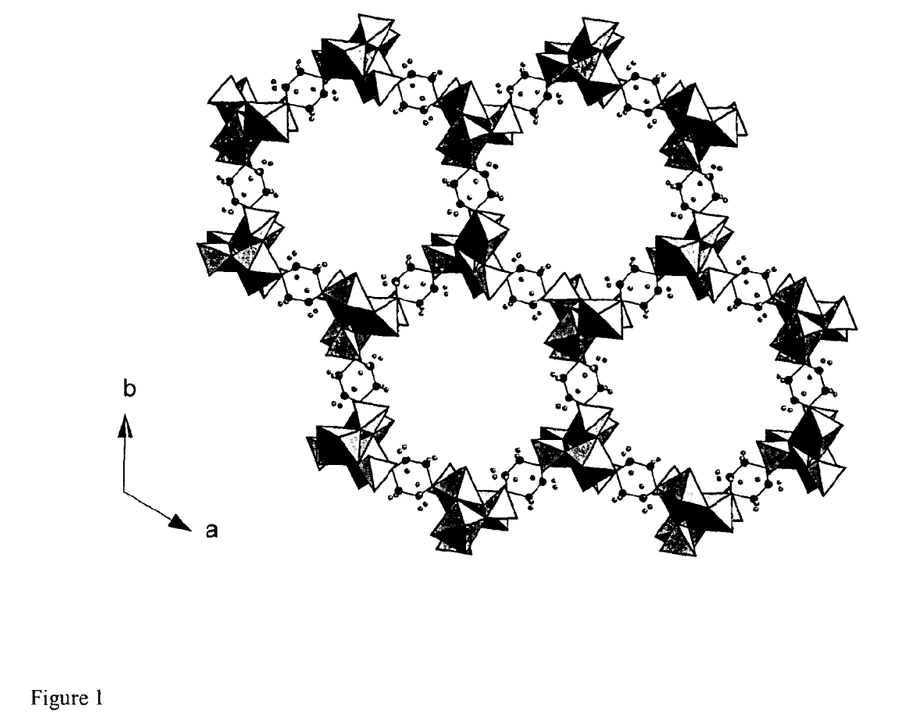
FIG. 1 shows the structure of background compound STA-12(Ni) projected down the channel axis. $NiO_5N$ octahedra are represented in dark grey, and $PO_3C$ tetrahedra in light grey.
Figure 5:
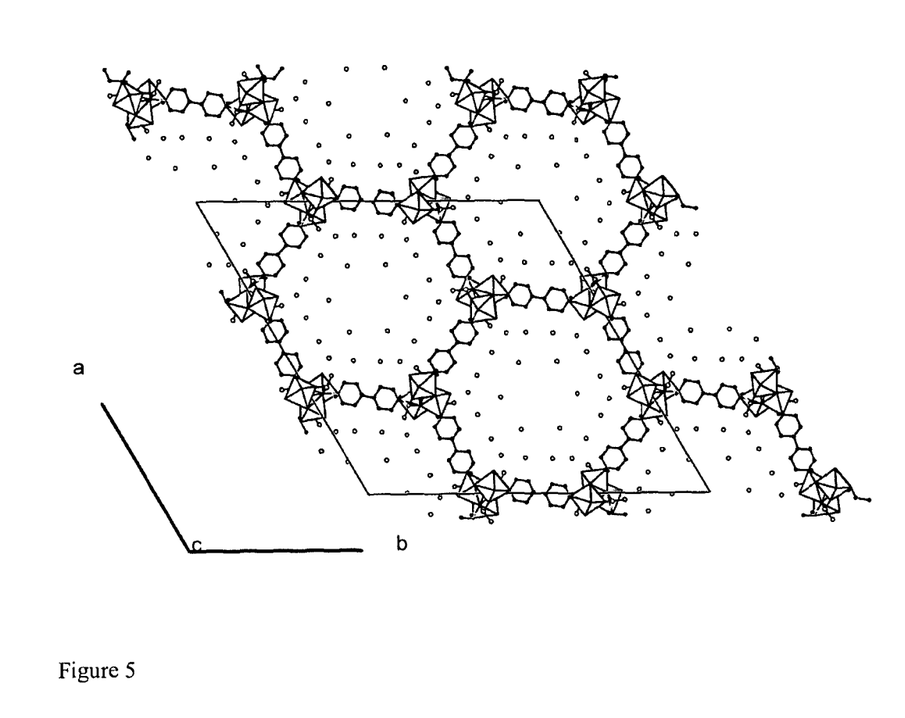
FIG. 5 shows the predicted structure of STA-16, viewed down the c axis (R-3, a=42.3 Å, c=6.24 Å).
Figure 6:
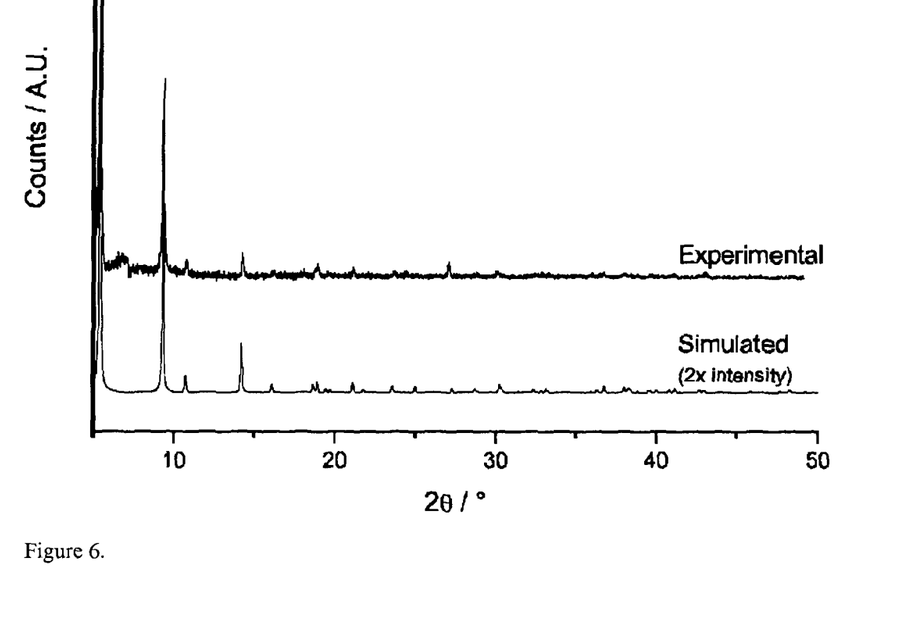
FIG. 6 shows a comparison of observed and simulated X-ray diffraction patterns for STA-16(Co) in hydrated form.

The composition, water loss behaviour, adsorption capacity and particularly the similar symmetry and c parameter but larger unit cell parameter in the a dimension compared to the STA-12 structure (unit cell STA-16(Co), R-3, a=42.3 Å, c=6.23 Å; STA-12(Ni), R-3, a=27.8 Å, c=6.24 Å) all suggest a model for STA-16(Co) consistent with the targeted isoreticular version of STA-12. A model was therefore constructed, starting from the structure of STA-12 and replacing N,N'-piperazinebismethylenephosphonate (L) groups with 4,4'-N,N'-bipiperidinyl bis(methylenephosphonate) (LL) units. The R-3 symmetry of the original solid can be retained, because both molecules can adopt the same local symmetry (with an inversion centre in L in the centre of the piperazine ring and in LL midway along the C—C bond linking the two piperidine rings). They also have the same arrangement of coordinating groups at each methylene phosphonate moiety (—$C_5H_9NCH_2PO_3$). Approximate positions were included for physisorbed water, estimated by comparison with the positions of water molecules in STA-12(Ni). The model (FIG. 5) can be compared directly with the structure of hydrated STA-12 (FIG. 1). FIG. 6 compares the observed diffraction pattern of STA-16(Co) with that simulated from the structural model prepared above. There is a reasonable agreement indicating that STA-16(Co) is the cobalt form of the isoreticular version of STA-12 with ligand LL.

The structure of STA-16(Co) in the hydrated form has extra large pores, some 1.8 nm in free diameter once the van der Waals radii of framework atoms and coordinated water molecules is taken into account. These pores fill with water, but this can be removed at room temperature under vacuum. Dehydration of STA-16(Co) results in loss of adsorbed water and a change of sample colour from purple to dark blue, consistent with a change of metal coordination from octahedral to 5-fold coordinated. This leads to some distortion away from rhombohedral symmetry, as observed by peak splitting in eth X-ray diffraction pattern, but the nitrogen adsorption data indicates that extra large pores are still present in the dehydrated form. STA-16(Co) therefore has permanent porosity approaching the mesoporous regime.

Figure 7:
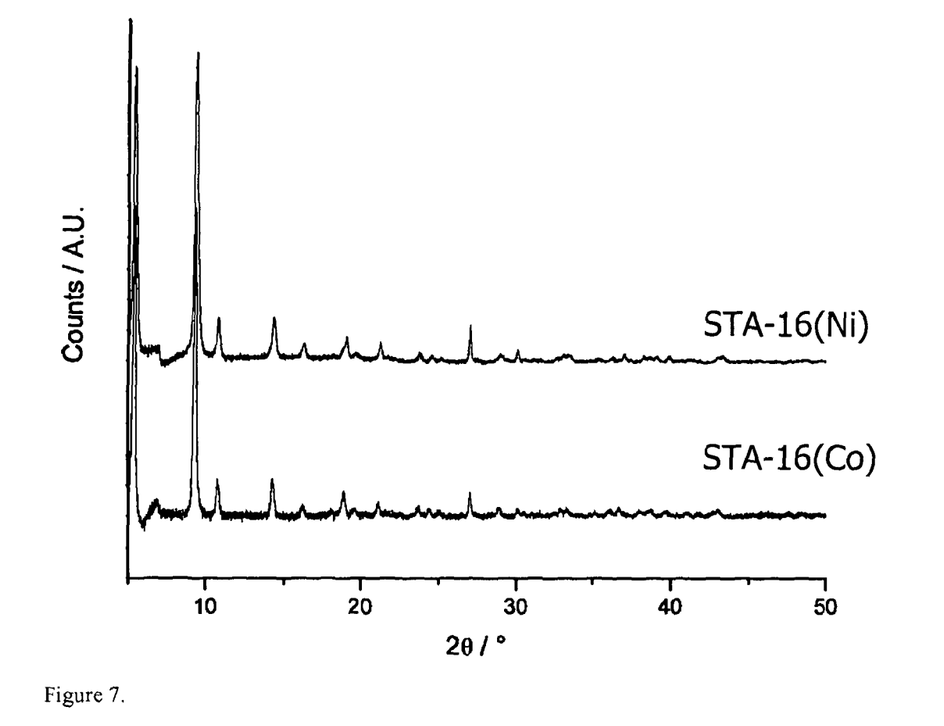
FIG. 7 Comparison of observed diffraction patterns of STA-16(Ni) in hydrated form with the diffraction pattern of STA-16(Co) in hydrated form.

Syntheses using nickel salts in place of cobalt salts indicate that STA-16(Ni) can also be obtained. FIG. 7 shows that it has been prepared. It is expected that STA-16 can also be made with the divalent metal cations $Mg^{2+}$, $Mn^{2+}$, $Fe^{2+}$ by analogy with what has been observed for STA-12.

In summary, STA-16 has the largest pore size of any reported crystalline metal phosphonate. The maximum dimension of pores available for molecular uptake (the free diameter of the channels is 1.8 nm) is comparable with the largest pore windows found in metal carboxylate MOFs, and physisorbed water molecules can be removed from the channels to leave permanent porosity of 0.62 cm$^3$ g$^{-1}$. The one dimensional honeycomb channel structure, typical of porous phosphonate MOFs, precludes the possibility of framework interpenetration (and subsequent reduction in porosity), and the material possesses the largest one dimensional channels of any MOF. The framework of STA-16 contains divalent metal cations in octahedral coordination, but upon dehydration the loss of one molecule per cation leaves coordinatively unsaturated sites.

Taken together, the structural features suggest possible applications in adsorption, storage and release, and catalytic conversions, particularly of large molecules. The coordinatively unsaturated sites can offer potential binding sites for polyamines (for enhanced $CO_2$ uptake) or for drug molecules with functional groups, to permit controlled release.

EXAMPLES

Example 1

Synthesis of Ligand

In a typical synthesis of the diphosphonic acid ligand, 4,4'-bipiperidine dihydrochloride (0.06 mol, 14.35 g, Alfa Aesar, 99%) was dissolved in an aqueous solution of phosphorous acid (12.8 g, 0.156 mol, Alfa Aesar, 97%), hydrobromic acid solution (41.6 ml, 48 wt. % aqueous solution, Aldrich) and distilled water (3.24 mol, 58.3 ml). Formaldehyde (26 ml, 0.35 mol, Alfa Aesar, 35 wt. % aqueous solution with 7-8% MeOH stabiliser) was added dropwise to the reaction over thirty minutes. The solution was refluxed at 120° C. for 20 hours following which a white precipitate formed. On cooling, solvent volume was reduced and the reaction mixture was cooled to 4° C. overnight to ensure complete precipitation. The product was separated by vacuum filtration, washed with a cold ethanol-water solution (90:10, 3×30 ml) and dried overnight at 40° C. Products were characterized by $^1$H, $^{13}$C, $^{31}$P NMR and single crystal X-ray diffraction. The mass of the final product was 21.75 g (yield: 92.4%). Elemental analysis gave C 33.02%, H 8.18%, N 6.74% (calculated for the crystallographic composition $C_{12}H_{26}N_2O_6P_2 \cdot 4H_2O$:C 33.65%, H 8.00%, N 6.54%).

$^1$H (400 MHz, $D_2O$/NaOH): δ=2.87 (d, $^2J_{Gem}$=11.7 Hz, 4H), 2.29 (d, $^2J(H-P)$=12.1 Hz, 4H), 1.98 (dd, $^2J_{Gem}$=11.2 Hz, $^3J_{Ax-Ax}$=11.2 Hz, 4H), 1.5 (d, $^2J_{Gem}$=12 Hz, 4H), 0.90 (m, 6H). $^{13}$C (400 MHz, $D_2O$/NaOH):=57.23 (d, $^1J(C-P)$=139.4 Hz), 54.61 (d, $^3J(C-P)$=7.5 Hz), 39.31 (s), 28.53 (s). $^{31}$P (400 MHz, $D_2O$/NaOH):=15.05 (t, $^2J(P-H)$=11.9 Hz).

Example 2

Synthesis of MOF

N,N'-4,4'-bipiperidinebis(methylenephosphonic acid) (H$_4$LL) (148.1 mg, 0.42 mmol) was mixed with constant stirring with distilled water (6.7 ml) in a 15 ml Teflon lined autoclave. To this was added potassium hydroxide solution (0.85 ml, 1.0M) and the solution stirred until the majority of the ligand was dissolved. To this solution, cobalt(II) acetate tetrahydrate (204.1 mg, 0.82 mmol) was added and a purple precipitate observed. The final reaction stoichiometry was 2.0:1.0:2.05:1000 (Co(AcO)$_2$:H$_4$LL:KOH:H$_2$O). The solution was aged at room temperature for 30 minutes, and the pH recorded as pH 8. The autoclave was then sealed and placed in a 220° C. oven for 65 hours. pH after reaction was 7. Solids were collected by vacuum filtration and washed with distilled water (20 ml). The prep for the nickel is identical except a longer reaction time is used and no base is added (Initial pH is 7, final pH is 5).

In addition to preparation of the pure cobalt- and nickel-versions of STA-16, the present inventors have also prepared mixed cobalt/nickel forms of STA-16, simply by co-addition of the relevant metal salts, typically acetates, in any ratios. In addition, the present inventors have also prepared STA-16 including other divalent cations, such as magnesium, into either the Co or Ni forms of the solid, at least up to Mg:Co or Mg:Ni ratios of 1:3. This was again achieved by adding mixtures of the metal salts, typically acetates, in the appropriate ratios, and employing the synthesis conditions described above for the pure Co or Ni materials.

TABLE 1

List of X-ray Powder Diffraction Peaks of STA-16(Co), measured in transmission mode using Fe Kα radiation (λ = 1.936042 Å), and showing dspacings, 2θ values and approximate relative intensities

| d-spacing /Å | 2θ/° | I(rel) |
|---|---|---|
| 20.583595 | 5.3911 | 100.00 |
| 11.867429 | 9.3576 | 76.77 |
| 10.286260 | 10.8000 | 21.47 |
| 7.771706 | 14.3104 | 18.04 |
| 6.855246 | 16.2356 | 11.44 |
| 6.143489 | 18.1316 | 8.82 |
| 5.896940 | 18.8965 | 11.98 |
| 5.681498 | 19.6200 | 8.52 |
| 5.278480 | 21.1346 | 9.22 |
| 4.954715 | 22.5331 | 6.97 |
| 4.712886 | 23.7057 | 7.60 |
| 4.580063 | 24.4036 | 7.13 |
| 4.493598 | 24.8806 | 6.07 |
| 4.333467 | 25.8156 | 5.53 |
| 4.226929 | 26.4779 | 5.47 |
| 4.141337 | 27.0354 | 9.03 |
| 3.879740 | 28.8966 | 6.19 |
| 3.731702 | 30.0695 | 5.49 |
| 3.685030 | 30.4595 | 4.85 |
| 3.623980 | 30.9854 | 4.40 |
| 3.564438 | 31.5163 | 4.37 |
| 3.479470 | 32.3067 | 4.26 |
| 3.461125 | 32.4827 | 4.45 |
| 3.413712 | 32.9466 | 4.64 |
| 3.378116 | 33.3038 | 4.51 |
| 3.202810 | 35.1845 | 3.43 |
| 3.126705 | 36.0700 | 3.83 |
| 3.076560 | 36.6786 | 4.16 |
| 3.050848 | 36.9989 | 3.17 |
| 2.976097 | 37.9633 | 3.51 |
| 2.960428 | 38.1720 | 3.24 |
| 2.935831 | 38.5043 | 3.28 |
| 2.919148 | 38.7331 | 3.62 |
| 2.850448 | 39.7054 | 3.27 |

The invention claimed is:

1. A porous isoreticular metal organic framework (MOF) comprising an organic compound co-ordinated to at least one metal selected from the group consisting of Co, Ni, Mg, Mn, Fe, Zn, Cd and Ru, wherein the organic compound is of the formula $PO_3CH_2X-Y-XCH_2PO_3$ wherein X is a substituted or unsubstituted heterocyclic amine containing one or more amine groups and Y forms a link between each group and is selected from the group consisting of a single bond, $-(CH_2)_n-$ where n is greater than or equal to 1, and a cyclic or heterocyclic substituted or unsubstituted ring structure.

2. The porous MOF according to claim 1 wherein the metal is selected from the group consisting of Co, Ni, Mn, Mg, Fe and mixtures thereof.

3. The porous MOF according to claim 1 wherein X is a fully saturated heterocyclic amine ring structure.

4. The porous MOF according to claim 1 wherein one or more available atoms on X is substituted by a functional group selected from the group consisting of $C_1$-$C_4$ alkyl, hydroxy, amino, nitro, and halo, where halo is selected from the group consisting of bromo, chloro, and iodo.

5. The porous MOF according to claim 1, wherein Y is a substituted or unsubstituted benzene ring.

6. The porous MOF according to claim 1, wherein the organic compound is 4,4'-N,N'-bipiperidinylbis(methylenephosphonate).

7. The porous MOF according to claim 1, wherein the MOF has large regular pore structures of at least 1.5 nm in diameter.

8. The porous MOF according to claim 1 which has a porosity of at least 0.5 $cm^3$ $g^{-1}$.

9. A method of making a MOF in accordance with claim 1, the method comprising the step of reacting a suitable base with at least one type of divalent metal cation and an organic acid of the formula:

in aqueous solution, wherein X and Y are as defined in claim 1, under hydrothermal reaction conditions, to thereby form a MOF.

10. The method according to claim 9, wherein the base is sodium or potassium hydroxide, and the base is added in an amount sufficient to adjust the pH of the solution and to assist dissolution of the acid form of the ligand.

11. The method according to claim 9, wherein the molar ratios of the starting materials range from: divalent metal cation:bisphosphonic acid: base: $H_2O$=0.5-2:1:0.5-2:1000-1500.

12. A method of uptake of one or more substances, the method comprising combining the porous MOF according to claim 1 with a substance selected from a gas, liquid and drug molecule, to thereby result in uptake of the substance in the pores of the MOF.

13. The method of claim 12, further comprising a step selected from the group consisting of storing, separating, controllably releasing and chemically reacting the substance taken up in the pores of the porous MOF.

14. The porous MOF of claim 3, wherein X is a piperidine ring, optionally substituted at one or more positions with a functional group selected from the group consisting of $C_1$-$C_4$ alkyl, hydroxy, amino, nitro, and halo.

15. The porous MOF of claim 5, wherein Y is a substituted benzene ring having one or more positions substituted with a nitro, amino, or halo group.

16. The porous MOF according to claim 1, having a porosity of at least 0.6 $cm^3$ $g^{-1}$ or higher.

17. A porous isoreticular metal organic framework (MOF) comprising an organic compound co-ordinated to at least one metal selected from the group consisting of Co, Ni, Mg, Mn, Fe, Zn, Cd and Ru, wherein the organic compound is of the formula wherein X is a substituted or unsubstituted heterocyclic amine containing one or more amine groups and Y forms a link between each group and is a substituted or unsubstituted benzene ring.

18. The porous MOF according to claim 17, wherein Y is a substituted benzene ring having one or more positions substituted with a nitro, amino, or halo group.

* * * * *